(12) United States Patent
Mahjoob

(10) Patent No.: US 8,845,771 B2
(45) Date of Patent: Sep. 30, 2014

(54) SYSTEM AND METHOD FOR CONVERTING SOLIDS INTO FUEL

(75) Inventor: Latif Mahjoob, Paramount, CA (US)

(73) Assignee: Latif Mahjoob, Paramount, CA (US)

( * ) Notice: Subject to any disclaimer, the term of this patent is extended or adjusted under 35 U.S.C. 154(b) by 626 days.

(21) Appl. No.: 12/178,516

(22) Filed: Jul. 23, 2008

(65) Prior Publication Data

US 2010/0018116 A1 Jan. 28, 2010

(51) Int. Cl.
*C01B 3/36* (2006.01)
*C10J 3/66* (2006.01)
*C10K 1/14* (2006.01)
*C10K 3/02* (2006.01)
*C10B 47/44* (2006.01)
*C10K 1/00* (2006.01)
*C10G 2/00* (2006.01)
*C01B 3/52* (2006.01)
*C10K 3/00* (2006.01)
*C01B 3/50* (2006.01)

(52) U.S. Cl.
CPC ............. *C10J 3/66* (2013.01); *C10G 2300/207* (2013.01); *C10G 2400/08* (2013.01); *C10J 2300/1693* (2013.01); *C10J 2300/0909* (2013.01); *C10K 1/143* (2013.01); *C01B 2203/0415* (2013.01); *C10K 3/023* (2013.01); *C10J 2300/0946* (2013.01); *C10B 47/44* (2013.01); *C10J 2300/1659* (2013.01); *C01B 2203/0485* (2013.01); *C10G 2300/1003* (2013.01); *Y02E 50/32* (2013.01); *C01B 2203/0475* (2013.01); *C10J 2300/1662* (2013.01); *C10K 1/004* (2013.01); *C10G 2/32* (2013.01); *C10J 2300/1665* (2013.01); *C10J 2300/1687* (2013.01); *C10G 2400/04* (2013.01); *C10G 2400/02* (2013.01); *C10J 2300/0923* (2013.01); *Y02E 50/18* (2013.01); *C01B 3/52* (2013.01); *C10K 3/006* (2013.01); *C01B 3/50* (2013.01)
USPC ...................................................... 48/197 R

(58) Field of Classification Search
CPC .................... C07C 29/1518; C10J 2300/1659; C10J 2300/1665; C10J 2300/0916; C10J 3/00; C10J 2300/0946; C10J 2300/1618; C10J 2300/0923; C10J 2300/1662; C10G 2300/1003; C01B 2203/062; C10K 1/004; F23G 5/027; F23G 5/0273; F23G 5/0276; Y02E 50/14
USPC .................................. 48/197 R–197 A, 127.1
See application file for complete search history.

(56) References Cited

U.S. PATENT DOCUMENTS 3,020,212 A 2/1962 Lantz
3,098,458 A 7/1963 Lantz, Jr.

(Continued)

FOREIGN PATENT DOCUMENTS

CN 1382202 A 11/2002
CN 101037952 A 9/2007
JP 2001-240878 A 9/2001

OTHER PUBLICATIONS

Tijmensen, M. et al. Exploration of the possibilities for production of Fischer Tropsch liquids and power via biomass gasification. Biomass & Energy, Aug. 2002, vol. 23, issue 2, pp. 130, 133, 134, 136, 138, Tables 4, 5, Figure 1.

(Continued)

*Primary Examiner* — Imran Akram
(74) *Attorney, Agent, or Firm* — Stoel Rives LLP

(57) ABSTRACT

A system for converting a solid fuel into a fuel including a pyrolytic unit for producing a pyro gas comprising hydrocarbons, a synthesis gas production unit for converting the pyro gas into a synthesis gas comprising a mixture of hydrogen and carbon monoxide, and a gas-to-liquid unit for converting the synthesis gas into a fuel.

21 Claims, 3 Drawing Sheets

(56) References Cited

U.S. PATENT DOCUMENTS

| | | | |
|---|---|---|---|
| 4,230,602 A | 10/1980 | Bowen et al. | |
| 4,436,532 A * | 3/1984 | Yamaguchi et al. | 48/209 |
| 4,465,556 A | 8/1984 | Bowen et al. | |
| 4,732,092 A * | 3/1988 | Gould | 110/229 |
| 5,744,668 A | 4/1998 | Zhou et al. | |
| 6,039,774 A * | 3/2000 | McMullen et al. | 48/102 A |
| 6,067,915 A | 5/2000 | Sharpe | |
| 6,538,166 B1 | 3/2003 | Mahjoob | |
| 6,604,474 B2 | 8/2003 | Zamansky et al. | |
| 7,008,459 B1 * | 3/2006 | Fraas et al. | 48/86 R |
| 7,014,668 B2 | 3/2006 | Golubkov et al. | |
| 2004/0024279 A1 * | 2/2004 | Mason | 588/226 |
| 2007/0100003 A1 * | 5/2007 | Holley et al. | 518/702 |
| 2008/0275278 A1 * | 11/2008 | Clark | 585/240 |
| 2009/0156695 A1 * | 6/2009 | Young | 518/702 |
| 2009/0221720 A1 * | 9/2009 | Belt et al. | 518/700 |
| 2010/0175320 A1 * | 7/2010 | Schuetzle et al. | 48/76 |
| 2010/0298449 A1 * | 11/2010 | Rojey | 518/700 |

OTHER PUBLICATIONS

Kagayama, et al., "Gasification of Solid Waste in Dual Fluidized-Bed Reactors," Tokyo University, Tokyo, Japan, American Chemical Society, pp. 525-540, Nov. 16, 1979.

Stoller, et al., "Lessons Learned from the 1970s Experiments in Solid Waste Conversion Technologies," Proceedings of the 17th Annual North American Waste-to-Energy Conference, pp. 1-15, May 18-20, 2009.

Gupta, et al., "Data Summary of Municipal Solid Waste Management Alternatives, vol. VI: Appendix D—Pyrolysis and Gasification of MSW," SRI International, Menlo Park, California, pp. 1-62, Oct. 1992.

* cited by examiner

SYSTEM AND METHOD FOR CONVERTING SOLIDS INTO FUEL

FEDERALLY SPONSORED RESEARCH

Not applicable.

REFERENCE TO MICROFICHE APPENDIX

Not applicable.

FIELD OF THE INVENTION

The present application relates to a system and method for converting solids into fuel, and more particularly, to a system and method for converting municipal solid waste, biosolid, waste rubber and plastic, sludge, wood, wood chips and coal into synthetic gas and thereafter converting the synthetic gas into liquid or gaseous fuel.

BACKGROUND OF THE INVENTION

Various waste-to-liquid fuel processes are currently available in the market utilizing embodiments of the Fischer-Tropsch ("F-T Process") process. The F-T process is a catalyzed chemical reaction in which synthesis gas (a mixture of carbon monoxide and hydrogen) is converted into liquid hydrocarbons of various forms. The synthesis gas may be produced from a variety of sources including, but not limited to, natural gas, coal, waste or any source of hydrocarbons. The reactions of the F-T process may include the following.

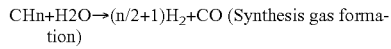

CHn+H2O→(n/2+1)H$_2$+CO (Synthesis gas formation)

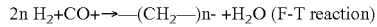

2n H$_2$+CO+→—(CH$_2$—)n- +H$_2$O (F-T reaction)

Many of the known waste-to-liquid processes involve direct flame gasification under high pressure while in the presence of steam to produce the synthesis gas. The chemical reaction involves the addition of some oxygen and is represented by the following chemical equation:

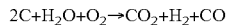

2C+H$_2$O+O$_2$→CO$_2$+H$_2$+CO

As indicated above, approximately 50% of the carbon is combusted and becomes CO$_2$, thereby producing a large amount of CO$_2$ emissions. As a result of the direct combustion of waste material and solid fuels, the gas may also contain harmful emissions such as nitrogen dioxides and sulfur dioxides. One of the disadvantages of these known processes is the resulting waste gas is diluted with nitrogen and CO$_2$, making direct combustion nearly impossible. Also, to clean the resulting waste gas in order to produce liquid fuel would be very costly. Furthermore, solids gasification produces ash having to be captured, separated and processed.

SUMMARY OF THE DISCLOSURE

A need therefore exists for a waste/solid fuel-to-liquid fuel system that deviates from the traditional Fischer-Tropsch method by performing pyrolysis in the absence of oxygen or air. As a result, the exemplary process produces low levels of CO$_2$ in both the pyrolytic process converting waste/solid fuel into H$_2$ and CO synthetic gas and the reforming process reacting the synthetic gas in a catalytic process to produce liquid fuel or other gases. The described process reduces the entrainment of small ash and carbon particles in the synthetic gas stream which is very clean and has a high calorific value. The exemplary pyrolytic process takes place in the absence of oxygen or air and, therefore, resultant emissions are reduced, including nitrogen dioxide and sulfur dioxide. Depending upon the sulfur content of the gasifying material some H$_2$S may be formed, but it is later removed from the gas prior to the final reformation process in the exemplary system.

An embodiment of the disclosure teaches a system for converting a solid fuel into a liquid or gaseous fuel, the system may include a pyrolytic unit for producing a pyro gas of hydrocarbons, a synthesis gas production unit for converting the pyro gas into a synthesis gas (a mixture of hydrogen and carbon monoxide), and a gas-to-liquid unit for converting the synthesis gas into a fuel. The pyrolytic unit may be a continuous pyrolytic unit. In some embodiments, the synthesis gas production unit is a steam reformer and the gas-to-liquid unit is a Fischer-Tropsch system. The system may also include a pyro gas cleanup unit including a carbon dioxide removal unit and/or a hydrogen sulfide removal unit for removing pollutants from the pyro gas. In other embodiments, the system also includes a synthetic gas cleanup unit including a hydrogen sulfide removal unit for removing pollutants from the synthesis gas. The system may also include a feed pretreatment unit. The continuous pyrolytic unit may be a low NOx emissions burner. The solid fuel may be municipal solid waste, municipal sludge, biosolid, rubber, plastic, coal, organic waste, inorganic waste, or combinations thereof and the liquid fuel may be diesel, gasoline, jet fuel, alcohols, methane or mixtures thereof.

Another embodiment of the disclosure is a method for converting a solid fuel into a liquid or gaseous fuel. The method may include the following: pyrolyzing the solid fuel into a low carbon dioxide pyro gas; reforming the low carbon dioxide pyro gas into a synthetic gas; and converting the synthetic gas into the liquid fuel. The solid fuel may be municipal solid waste, municipal sludge, biosolid, rubber, plastic, coal, organic waste, inorganic waste, or combinations thereof. The method may also include removing pollutants from the low carbon dioxide pyro gas and/or removing pollutants from the synthetic gas. The liquid fuel may be diesel, gasoline, jet fuel, alcohols, methane or mixtures thereof. In some embodiments, pyrolyzing the solid fuel may be by continuous indirect flame pyrolysis A steam reformer may reform the low carbon dioxide pyro gas. A Fischer-Tropsch reactor may convert the synthetic gas. In some embodiments, the pollutants include H$_2$S, COS, CO$_2$, SO$_2$, or mixtures thereof. The pollutants may be removed by scrubbing the pyro gas and capturing the pollutants. In some embodiments, the method also includes pre-treating the solid fuel.

BRIEF DESCRIPTION OF THE DRAWINGS

Embodiments of the present application are illustrated by way of example in the accompanying figures, in which like reference numbers indicate similar elements, and in which.

DETAILED DESCRIPTION

The present application describes and illustrates exemplary embodiments for converting various solids, including but not limited to municipal solid waste, biosolids, waste rubber and plastic, sludge and coal, into liquid fuel such as diesel fuel, gasoline, jet fuel, methanol, ethanol, other alcohols or simply methane gas. Sludge is a well known term in the art and is often described as the residual semi-solid material left from industrial, water treatment, or wastewater treatment processes, including biosolids. Municipal solid waste (MSW), sludge and coal are collectively referred to in the present application as "solid fuel". As will be appreciated by a person having ordinary skill in the art, the exemplary embodiments of the present application are not limited to these solids and therefore a variety of other solids, such as MSW, organic waste such as wood and agricultural waste, inorganic waste such as plastic, rubber, and coal can be converted into liquid fuel using the systems and methods of the present application.

Figure 1:
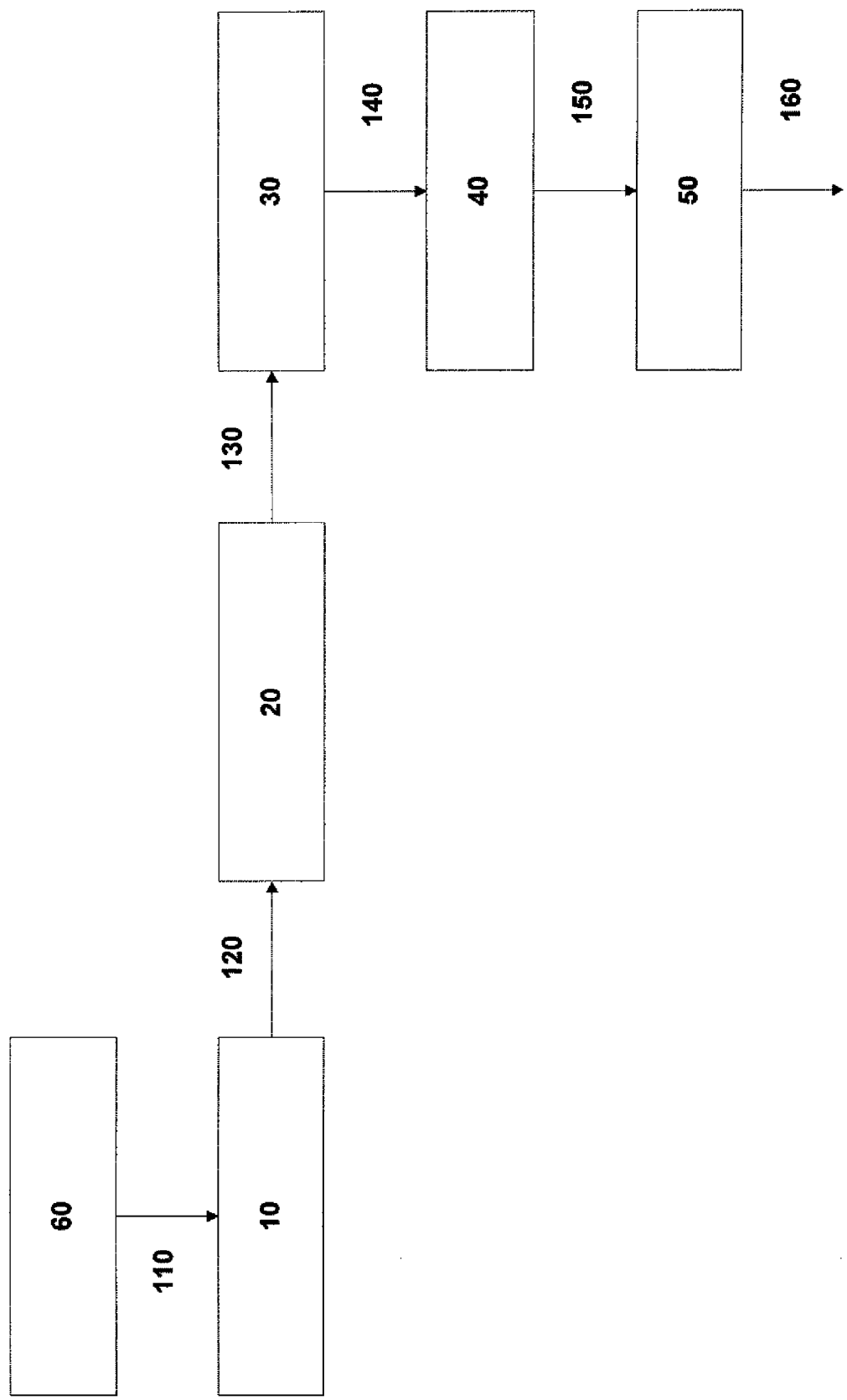
FIG. 1 shows an exemplary process flow diagram of a system of and a process for converting municipal sold waste, biosolid, waste rubber and plastic, sludge and coal into liquid fuel according to an exemplary embodiment of the application.
Figure 2:
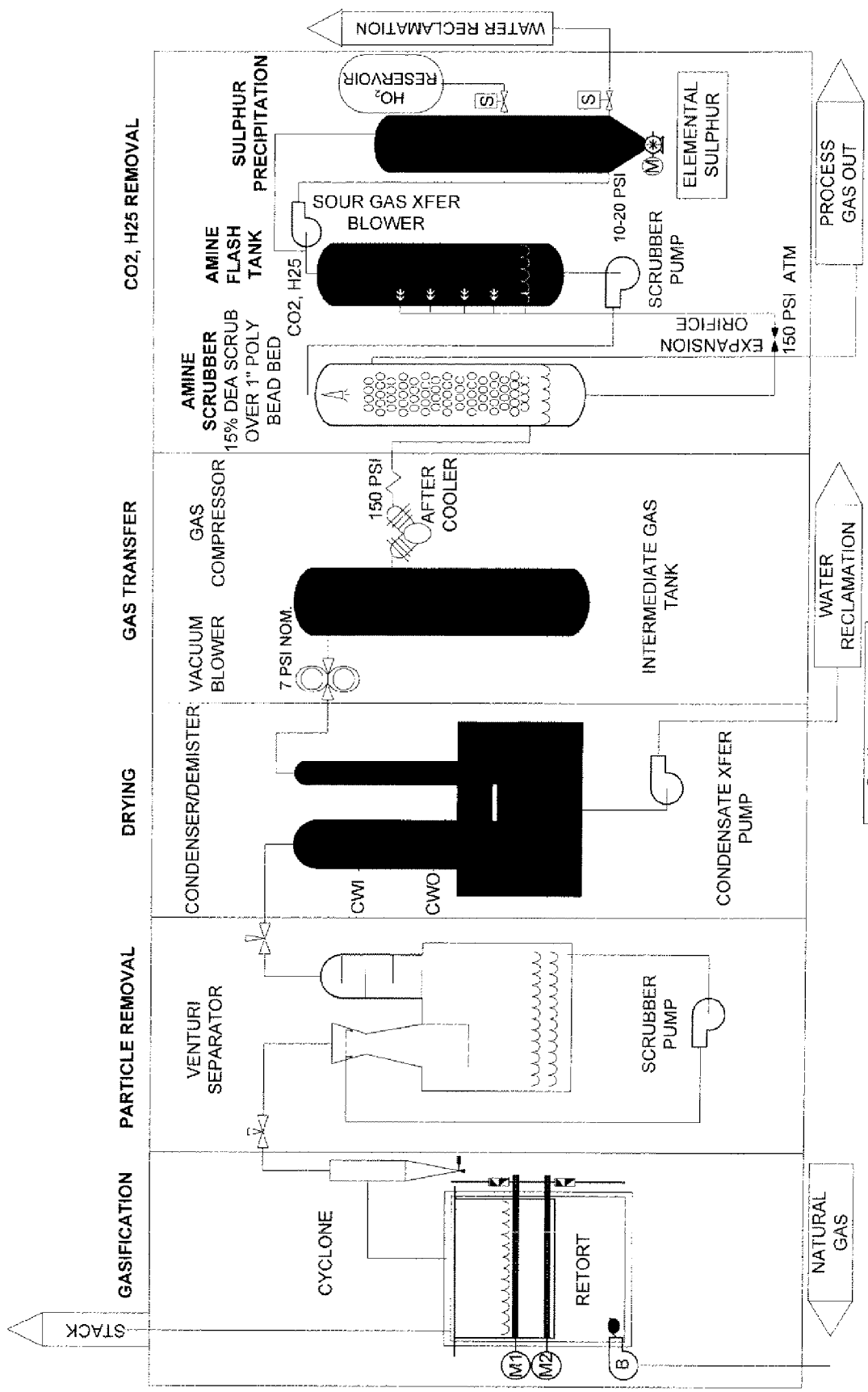
FIG. 2 shows an embodiment of a detailed flow diagram for the gasification skid.
Figure 3:
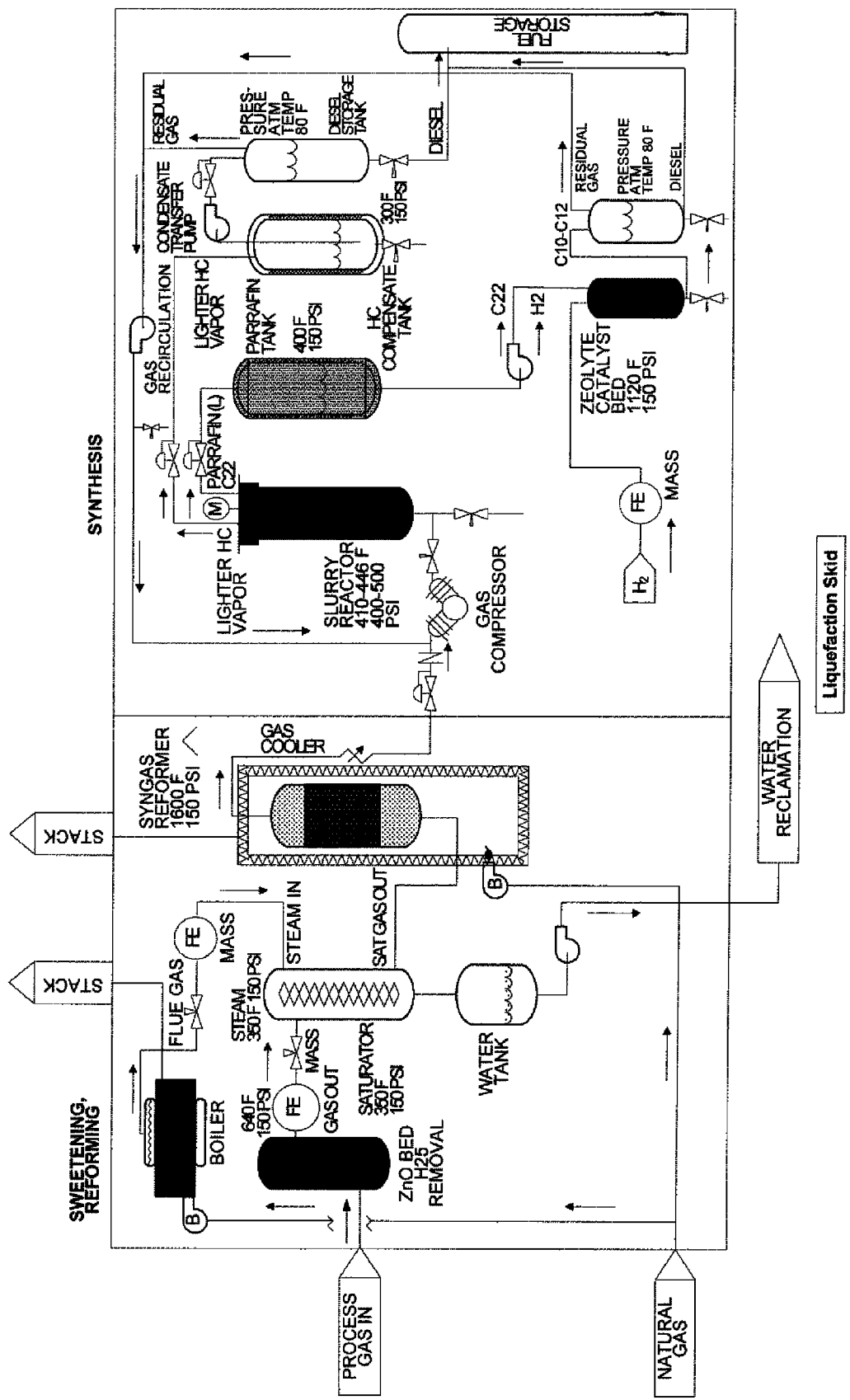
FIG. 3 shows an embodiment of a detailed flow diagram for the liquefaction skid.

The exemplary systems and methods are described herein with reference to FIGS. 1, 2 and 3. As can be seen in FIG. 1, the system comprises a pyrolysis unit 10, a pyro gas cleanup unit 20, a synthesis gas production unit 30, a synthetic gas cleanup unit 40, and a gas to liquid production unit 50. In some embodiments, a feed treatment unit 60 is also included. A basic arrangement for the processing units used in this disclosure can be readily understood by a review of the flow scheme presented in FIG. 1. Although FIG. 1 and this description makes no mention of many pumps, compressors, receivers, condensers, reboilers, instruments, and other well known items of processing equipment in order to simplify the explanation of the disclosure. In some embodiments, the system comprises a gasification skid and a liquefaction skid. FIGS. 2 and 3 provide a preferred embodiment of the disclosure incorporating some of the preferred equipment within the gasification skid and the liquefaction skid including the following units- the pyrolysis unit 10, the pyro gas cleanup unit 20, the synthesis gas production unit 30, the synthetic gas cleanup unit 40, and the gas to liquid production unit 50. In some embodiments, the gasification skid includes the pyrolysis unit 10 and the pyro gas cleanup unit 12, and the liquefaction skid includes the synthesis gas production unit 30, the synthetic gas cleanup unit 40, and the gas to liquid production unit 50.

An exemplary method of using the system as shown in FIG. 1, provides a solid fuel 110 being fed to the pyrolysis unit 10. The solid fuel 110 may be municipal solid waste, biosolid, waste rubber and plastic, municipal sludge, coal, organic materials, or combinations thereof. In some embodiments, the pyrolysis unit 10 includes a retort and a separator. In a preferred embodiment, the retort is sealed and equipped with air tight inlet and outlet valves in order to prevent the introduction of air into the pyrolysis unit during operation. In a preferred embodiment, the retort is manufactured by American Combustion Technologies, Inc. (Paramount, Calif.). As the solid fuel 110 travels through the retort, indirect heat is applied by the one or more gas burners causing the solid fuel 110 to be converted to a pyro gas 120 including steam. In an exemplary embodiment of the present application, the temperature in the pyrolysis unit is from about 800° F. to about 1300° F. and a negative pressure is maintained from about −0.20" to about −1.00" water column (W.C.). In a preferred embodiment, the one or more gas burners are of low $NO_x$ emission type burners, specifically the AHS or SLE series meeting below 30 and 9 ppm $NO_x$ emissions throughout the firing rates, available from American Combustion Technologies, Inc. (Paramount, Calif.). In a preferred embodiment, one or more gas burners are powered by natural gas, propane, pyro gas, or pyro oil. In a preferred embodiment, the one or more burners meet the South Coast Air Quality Management District requirements.

In some embodiments, the solid fuel 110 moves through the retort using stainless steel augurs. The speed of augurs is controlled allowing the travel time through the retort to be different depending on the specific type of solid fuel 110 being gasified. In an exemplary embodiment, the travel time is approximately one hour.

Gas and water evaporate from the solid fuel 110 in the retort and are passed to a separator to separate any liquid, particles and sludge from the gas stream. In a preferred embodiment, the separator is a cyclone separator. Cyclone separators are well known in the art and are therefore not described in detail in the present application. The cyclone separator is capable of removing about 99.9% of all free liquids and solids being approximately 5 microns or larger and is effective for the removal of solids, such as phaltines and iron sulphides. The majority of the solid collected is carbon and the amount is minor.

In some embodiments, upon exiting the pyrolysis unit 10, the pyro gas 120 enters the pyro gas clean-up unit 20 which removes pollutants therefrom, producing a processed gas 130. Pollutants may include, but are not limited to, ash (including tar sludge and particles), hydrogen sulfide ($H_2S$), carbon oxide sulfide (COS), carbon dioxide ($CO_2$) and mixtures thereof. The pyro gas clean-up unit 20 may include several exemplary sub-systems, such as but not limited to, a particle removal sub-system, a drying sub-system, a gas transfer sub-system, and a $CO_2/H_2S$ removal sub-system.

In some embodiments, the particle removal sub-system is a venturi separator. Venturi separators operate as a wash system to remove any dust mixed with the gas. Venturi separators may also separate, if present, water vapors and most of the $SO_2$ and COS from the pyro gas during the wash process. If the gas includes $H_2S$, some of the $H_2S$ will be removed in the venturi separator, however, some of the $H_2S$ will be stripped in the $CO_2/H_2S$ removal sub-system, described below in more detail. Venturi separators or scrubbers are well known in the art and typically consist of a venturi-shaped inlet and separator. In a preferred embodiment, the venturi separator is manufactured by American Combustion Technologies, Inc. (Paramount, Calif.).

In some embodiments, after exiting the particle removal subsystem, the gas travels through the drying sub-system which may be a condenser/demister which is operable as a heat exchanger for separating all the liquids from the gas. Condenser/demisters are well known in the art and are therefore not described in detail in the present application.

In some embodiments, after exiting the drying subsystem, the gas enters the gas transfer sub-system. The gas transfer sub-system may include a vacuum blower, an intermediate gas tank, a gas compressor, an after-cooler, or any combination thereof, all of which are well known in the art and are therefore not described in detail in the present application.

In some embodiments, from the gas transfer sub-system, the compressed gas enters the $CO_2/H_2S$ removal sub-system. Although the pyrolysis unit 10 does not produce a great deal of $CO_2$, from about 1% to about 15%, the $CO_2/H_2S$ removal sub-system further reduces the $CO_2$ emissions to between about 0.1% to 3%. In a preferred embodiment, the $CO_2/H_2S$ removal sub-system also reduces the amount of $H_2S$ to below 7 ppb.

In some embodiments, the $CO_2/H_2S$ removal sub-system may include an amine scrubber, an amine flash tank, a sulphur precipitation unit, a sulphur stripper, a saturator, or any combination thereof all of which are well known in the art and are therefore not described in detail in the present application. After the pyro gas clean-up unit, the processed gas 130 contains between about 0 and 7 ppb of $H_2S$, and 0 to 3% $CO_2$ which may be captured and stored. It should be noted that none of the water is wasted in the pyrolysis unit 10 or the pyro gas clean-up unit 20. Excess water is recaptured, cleaned and reused in the subsystems.

In an exemplary embodiment of the present application, the processed gas 130 is saturated with steam having a temperature of about 350° F. and a pressure of about 50 psi. In some embodiments, the pressure range of steam may be from about 120 psig to about 200 psig. The saturated processed gas 130 is fed to a synthesis gas production unit 30. The synthesis gas production unit 30 produces a synthesis gas 140 typically having $H_2/CO$ ratios of 2:1, 3:1 and 4:1. The $H_2/CO$ ratios may range from 1 to 6 dependent upon the requirements for the final product. In some embodiments, the processed gas 130 is preheated, for example, to about 1600° F. or slightly higher and has a pressure of approximately 150 psi, in order to reform the hydrocarbons to CO and $H_2$ within the synthesis gas production unit 30.

As will be appreciated by a person having ordinary skill in the art, a steam reforming reaction in the synthesis gas production unit 30 includes reacting the hydrocarbons of the processed gas 130 with steam to form hydrogen, carbon monoxide, methane and carbon dioxide. In general. reforming of hydrocarbon through steam reforming involves a large-scale endothermic reaction. In some embodiments, the synthesis gas production unit 30 includes a fixed bed reactor. In other embodiments, the synthesis gas production unit 30 includes a slurry reactor.

The proper amount of water should be employed within the synthesis gas production unit 30. The use of low amounts of water may result in low $H_2$ production and heavier liquid fuels being produced in the gas-to-liquid production unit 50. Larger amounts of steam injection may result in higher levels of $H_2$ production which is later used to reform the CO2 back into CO.

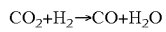
$$CO_2+H_2\rightarrow CO+H_2O$$

Low amounts of $H_2$ in the synthesis gas 140 may also indicate the lack of excess steam during the synthesis gas production unit 30. Steam helps prevent the formation of carbon on the catalyst, in a fixed bed reactor, within the synthesis gas production unit 30 which may eventually deactivate the catalyst. In some embodiments of fixed bed reactors, it is helpful if a small amount of solvent is injected into the synthesis gas production unit 30 to increase the life of the catalyst and prevent contamination by the carbon formation.

The conditions within the synthesis gas production unit 30 are monitored to obtain a uniform synthesis gas 140 composition of CO and $H_2$. In some embodiments, the CO and $H_2$ are separated and mixed back together in a pre-determined ratio in order to obtain a uniform synthesis gas 140 composition. The formation of synthesis gas 140 takes place according to the following chemical reactions:

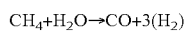
$$CH_4+H_2O\rightarrow CO+3(H_2)$$

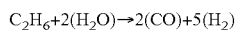
$$C_2H_6+2(H_2O)\rightarrow 2(CO)+5(H_2)$$

This process can be applied to all of the hydrocarbons within the processed gas 130.

The synthesis gas 140 may contain some nitrogen. The amount of nitrogen is very low and may not have to be removed. However, if the nitrogen is taken out prior to the gas to liquid production unit 50, the fuel product 160 will not contain any nitrogen related liquid products. In some embodiments, the synthesis gas 140 is processed in the synthesis gas clean-up unit 40 producing a processed syngas 150. In some embodiments, the synthesis gas clean-up unit 40 removes pollutants from the synthesis gas 140. In an exemplary embodiment, the synthesis gas clean-up unit 40 includes a zinc oxide bed to remove any remaining $H_2S$.

In a preferred embodiment, the processed syngas 150 is pressurized and heated in the gas-to-liquid production unit 50. In some embodiments, the gas-to-liquid production unit 50 includes one or more reactors. When using two reactors, the first reactor pressure ranges from about 300 to 1000 psig, more preferably from about 500 to 750 psig and the temperature is below 600° F. In a preferred embodiment, the first reactor operates at a temperature of about 520° F. After the first reactor, the gas is cooled and pressurized to a pressure ranging from about 300 to 1000 PSIG. The pressurized gas is then heated and passed through a second reactor. In some embodiments, the first reactor is a slurry reactor which employs a cobalt or iron oxide catalyst and the temperature is kept constant to maximize the liquid production. In some embodiments, 50% wax is produced in the slurry reactor which may be further processed into diesel fuel via hydrogenation. In some embodiments, the wax includes components having carbon numbers greater than 40. In a preferred embodiment, the slurry reactors operate at pressures ranging from about 300 psig to about 500 psig and temperatures ranging from about 430 to about 460° F.

In some embodiments, the second reactor employs a nickel based catalyst which increases the formation of alcohols and methane depending on the hydrogen and carbon monoxide ratios of the feed. In some embodiments, a second catalyst is necessary to dehydrate the alcohol into diesel or light liquid fuels. In an alternate embodiment, iron oxide or cobalt catalysts may be used to produce diesel or light liquid fuels.

Modifying the ratio of $H_2$ to CO within the synthesis gas production unit 30 will impact the fuel product 160 from the gas-to-liquid unit 50 depending on the pressure and temperature of the gas and type of catalyst being used in the gas-to-liquid unit 50. The fuel product 160 is separated into gasoline, jet fuel, alcohols, and diesel fuel using a distillation column (not shown). In some embodiments, the fuel product 160 may be gaseous. The basic range of the production of the fuels within the fuel product 160 may be approximated as:

| | |
|---|---|
| Diesel fuel | 70% |
| Gasoline, jet fuel and light solvents | 20% |
| Oxygenates ($CH_3OH$, etc.) | 10% |

In some embodiments, after the fuel product 160 have been properly separated, no further processing will be necessary to qualify them as a standard fuel.

In some embodiments, the fuel product 160 may contain some water which was either produced during the reaction of $CO_2$ with $H_2$ or resulted from that portion of the steam that did not participate in the reaction. This water is separated from the fuel and fuel is further cleaned and separated before use. The water separation process is simple and can take place either through a flash separation process or through the use of a distillation column. Both are common and easy to design and build.

In some embodiments, at least 70% of the processed syngas 150 gas is transformed into fuel product 160. In a preferred embodiment, over 90% of the processed syngas 150 gas is transformed into fuel product 160. In some embodiments, the lighter hydrocarbons of the fuel product 160 may be recycled to the synthesis gas production unit 30 to increase the formation of fuel product 160.

In some embodiments, the solid fuel 110 is the product from a feed pretreatment unit 60 to destroy caking properties prior to entering the pyrolytic process 10.

As will be understood by one skilled in the art, the present application is not limited to the precise exemplary embodiments described herein and various changes and modifications may be effected without departing from the spirit or scope of the application. For example, elements and/or features of different illustrative embodiments may be combined with each other, substituted for each other, and/or expanded upon within the scope of the present disclosure and the appended claims. In addition, improvements and modifications which become apparent to persons of ordinary skill in the art after reading the present disclosure and appended drawings are deemed within the spirit and scope of the present application.

What is claimed:

1. A method for converting a solid fuel into a fuel product, comprising:
   gasifying in only a single reactor a solid fuel into a pyro gas comprising less than about 15% carbon dioxide, the gasifying being conducted without introduction of an oxygen, air, or steam stream at about 800° F. to about 1300° F. and at a negative atmospheric pressure, wherein the reactor is a retort comprising one or more augers and is sealed and equipped with air tight inlet and outlet valves configured to prevent introduction of air into the reactor during operation, and wherein the solid fuel is gasifying while the one or more augers move it through the retort;
   removing pollutants from the pyro gas by scrubbing and by capturing the pollutants with a particle removal subsystem, wherein removing pollutants from the pyro gas comprises removing carbon dioxide, hydrogen sulfide, or both carbon dioxide and hydrogen sulfide to form a scrubbed pyro gas;
   reforming the scrubbed pyro gas into a synthetic gas; and
   converting the synthetic gas into a fuel product.

2. The method of claim 1, wherein the solid fuel comprises municipal solid waste, municipal sludge, biosolid, rubber, plastic, coal, organic waste, inorganic waste, medical waste, by-products thereof, or combinations thereof.

3. The method of claim 1, further comprising removing pollutants from the synthetic gas to form a processed synthetic gas.

4. The method of claim 1, wherein the fuel product is a wax, liquid, a gas, or a combination thereof.

5. The method of claim 4, wherein the liquid comprises diesel, gasoline, jet fuels, alcohols, or mixtures thereof.

6. The method of claim 1, wherein gasifying the solid fuel comprises continuous indirect flame pyrolysis.

7. The method of claim 1, wherein reforming the scrubbed pyro gas comprises utilizing a steam reformer.

8. The method of claim 1, wherein converting the synthetic gas comprises a Fischer-Tropsch reactor.

9. The method of claim 1, wherein the pollutants comprise $H_2S$, COS, $CO_2$, $SO_2$, or mixtures thereof.

10. The method of claim 1, further comprising pre-treating the solid fuel.

11. The method of claim 1, wherein the gasifying the solid fuel further comprises continuously gasifying the solid fuel.

12. The method of claim 1, wherein the pyro gas comprises from about 1% to about 15% carbon dioxide.

13. The method of claim 1, wherein the gasifying occurs at about 1300° F.

14. The method of claim 1, wherein converting the synthetic gas into the fuel comprises reacting the synthetic gas with a catalyst to form a liquid fuel.

15. The method of claim 14, wherein the catalyst comprises a nickel catalyst.

16. The method of claim 14, wherein the catalyst comprises a cobalt catalyst.

17. The method of claim 1, further comprising controlling a speed of the one or more augers so that a travel time of the solid fuel through the retort is approximately one hour.

18. A method for converting a solid fuel into a fuel, comprising:
   gasifying in only a single reactor a solid fuel into a pyro gas comprising less than about 15% carbon dioxide, the gasifying being conducted without introduction of an oxygen, air, or steam stream at about 800° F. to about 1300° F., utilizing continuous indirect heat, and at a negative atmospheric pressure, wherein the reactor is a retort comprising one or more augers and is sealed and equipped with air tight inlet and outlet valves configured to prevent introduction of air into the reactor during operation, and wherein the solid fuel is gasifying while the one or more augers move it through the retort;
   saturating the pyro gas with steam prior to introducing the pyro gas into a steam Reformer;
   reforming the pyro gas into a synthetic gas in the steam reformer, wherein the synthetic gas comprises carbon monoxide and hydrogen; and
   converting the synthetic gas into a fuel product.

19. The method of claim 18, wherein the gasifying occurs at about 1300° F.

20. The method of claim 18, wherein the synthetic gas comprises a molar ratio of carbon monoxide to diatomic hydrogen of about 1:1 to about 1:6.

21. The method of claim 18, wherein the steam is at a pressure of about 120 pounds per square inch gauge ("psig") to about 200 psig.

* * * * *